United States Patent
Tsujino et al.

(10) Patent No.: US 10,504,680 B2
(45) Date of Patent: Dec. 10, 2019

(54) X-RAY GENERATION TUBE, X-RAY GENERATION APPARATUS, AND RADIOGRAPHY SYSTEM

(71) Applicant: CANON KABUSHIKI KAISHA, Tokyo (JP)

(72) Inventors: Kazuya Tsujino, Tokyo (JP); Yasuo Ohashi, Hadano (JP)

(73) Assignee: Canon Kabushiki Kaisha, Tokyo (JP)

( * ) Notice: Subject to any disclaimer, the term of this patent is extended or adjusted under 35 U.S.C. 154(b) by 400 days.

(21) Appl. No.: 15/598,106

(22) Filed: May 17, 2017

(65) Prior Publication Data

US 2017/0338077 A1    Nov. 23, 2017

(30) Foreign Application Priority Data

May 23, 2016  (JP) .................................. 2016-102863

(51) Int. Cl.
| | |
|---|---|
| *H01J 35/30* | (2006.01) |
| *H01J 35/14* | (2006.01) |
| *G01N 23/04* | (2018.01) |
| *H01J 35/16* | (2006.01) |
| *H01J 35/08* | (2006.01) |

(52) U.S. Cl.
CPC .............. *H01J 35/14* (2013.01); *G01N 23/04* (2013.01); *H01J 35/16* (2013.01); *H01J 35/116* (2019.05); *H01J 2235/165* (2013.01)

(58) Field of Classification Search
CPC .. G01N 23/04; H01J 2235/165; H01J 35/116; H01J 35/14; H01J 35/16; H01J 35/186; H01J 35/30; H01J 35/32; H01J 35/08; H01J 2201/342; H01J 2235/086; H01J 35/065; H01J 2235/166; H01J 35/00; H01J 35/305; H01J 2235/081; H01J 2235/1216; H01J 35/025; H01J 35/28; H01J 35/06; H01J 2235/168; H01J 2235/068; H05G 1/10; H05G 1/06; H05G 1/32

USPC ...................... 378/137, 138, 119, 121, 145
See application file for complete search history.

(56) References Cited

U.S. PATENT DOCUMENTS

| | | | |
|---|---|---|---|
| 7,428,298 B2 * | 9/2008 | Bard ....................... | H01J 35/14 378/138 |
| 9,916,961 B2 * | 3/2018 | Canfield ................. | H01J 35/06 |
| 2009/0154650 A1 * | 6/2009 | Tanabe ................. | A61N 5/1042 378/137 |
| 2014/0064456 A1 | 3/2014 | Zou et al. | |
| 2014/0328467 A1 * | 11/2014 | Weigand ............. | A61N 5/1001 378/137 |

FOREIGN PATENT DOCUMENTS

| | | |
|---|---|---|
| CN | 1698175 A | 11/2005 |
| CN | 101103431 A | 1/2008 |

(Continued)

*Primary Examiner* — Irakli Kiknadze
(74) *Attorney, Agent, or Firm* — Canon U.S.A., Inc. IP Division

(57) ABSTRACT

An X-ray generation tube including a magnetic deflection portion configured to deflect an electron beam to reduce lines of magnetic force extending to the outside of the tube, where a subject is arranged, by placement of a magnetic shielding portion including a portion that is closer to an anode than the magnetic deflection portion in a tube axial direction and that is closer to the tube center axis than the magnetic deflection portion in a tube radial direction.

20 Claims, 9 Drawing Sheets

(56) References Cited

FOREIGN PATENT DOCUMENTS

| | | |
|---|---|---|
| CN | 104756222 A | 7/2015 |
| CN | 105575747 A | 5/2016 |
| JP | 2009-43741 A | 2/2009 |
| JP | 2009238600 A | 10/2009 |
| JP | 2015114132 A | 6/2015 |
| WO | 2014125702 A1 | 8/2014 |

* cited by examiner

FS0: WITHOUT MAGNETIC DEFLECTION PORTIONS 6
FS1: WITH MAGNETIC DEFLECTION PORTIONS 6

FS50: WITHOUT MAGNETIC DEFLECTION PORTIONS 6
FS51: WITH MAGNETIC DEFLECTION PORTIONS 6

X-RAY GENERATION TUBE, X-RAY GENERATION APPARATUS, AND RADIOGRAPHY SYSTEM

BACKGROUND

Field of the Disclosure

The present disclosure relates to an X-ray generation apparatus that can be used in nondestructive radiography and the like and to a radiography system including the X-ray generation apparatus.

Description of the Related Art

There is a known transmission X-ray generation tube used in an X-ray generation apparatus in, for example, an X-ray nondestructive inspection system. The transmission X-ray generation tube includes a transmission target including a target layer arranged on a side on which electron beams are emitted and a supporting substrate that supports the target layer. The transmission target constitutes an anode portion in the transmission X-ray generation tube and allows X rays generated in the target layer to pass through the supporting substrate and radiate outside the tube.

There is a known transmission X-ray generation tube that enables radiography at high magnification by reducing the distance between an object and an electronic focus by taking the form in which the transmission X-ray generation tube is housed in a container such that a transmission target is arranged as an end window. Meanwhile, the thickness of the target layer in the transmission X-ray generation tube is set at no more than approximately 15 µm in consideration of self-absorption of X rays restricted in the thickness direction of the target layer.

Heat load generated at the electronic focus dissipates from the thickness direction of the target layer toward the substrate and the surface direction of the target layer, but the quantity of heat transfer is limited. Thus, heat damage to the target layer may restrict the life of the transmission target.

Japanese Patent Laid-Open No. 2009-43741 discloses an X-ray generation tube including a magnetic deflection portion that generates lines of magnetic force that exert Lorentz force on electronic beams. This patent literature also discloses moving the position of an electronic focus by deflecting an electronic beam by using the Lorentz force and additionally discloses recovering the performance of X-ray generation by moving the position of the electronic focus to a region that is not thermally damaged.

SUMMARY

The present disclosure provides an X-ray generation tube including a cathode, an anode, an insulating tube, and at least one magnetic deflection portion. The cathode includes an electronic gun including an electron emission portion and an electrostatic lens electrode. The anode includes a target layer and a supporting substrate configured to support the target layer and allow an X ray generated in the target layer to pass therethrough. The insulating tube surrounds and extends along a tube center axis and includes a first end and a second end configured to be connected to the cathode and the anode, respectively. The magnetic deflection portion is disposed outside the insulating tube in a tube radial direction and arranged between the electron emission portion and the target layer in a tube axial direction. The X-ray generation tube further includes a magnetic shielding portion including a portion that is closer to the anode than the magnetic deflection portion in the tube axial direction and that is closer to the tube center axis than the magnetic deflection portion in the tube radial direction.

The present disclosure provides an X-ray generation apparatus including an X-ray generation tube. The X-ray generation tube includes a cathode, an anode, and an insulating tube. The cathode includes an electronic gun and a cathode member configured to hold the electronic gun. The anode includes a transmission target configured to be irradiated with electrons and generate an X ray and an anode member configured to hold the transmission target. The insulating tube surrounds and extends along a tube center axis and includes a first end and a second end configured to be connected to the cathode and the anode, respectively.

The X-ray generation apparatus further includes at least one magnetic deflection portion, a magnetic shielding portion, and a container. The magnetic deflection portion is disposed outside the insulating tube in a tube radial direction and arranged between the cathode and the anode in a tube axial direction. The magnetic shielding portion is includes a portion that is closer to the anode than the magnetic deflection portion in the tube axial direction and that is closer to the tube center axis than the magnetic deflection portion in the tube radial direction. The container is configured to house the X-ray generation tube and the magnetic shielding portion. The magnetic shielding portion is fixed to the container.

Further features of the present disclosure will become apparent from the following description of exemplary embodiments with reference to the attached drawings.

DESCRIPTION OF THE EMBODIMENTS

Figure 1A:
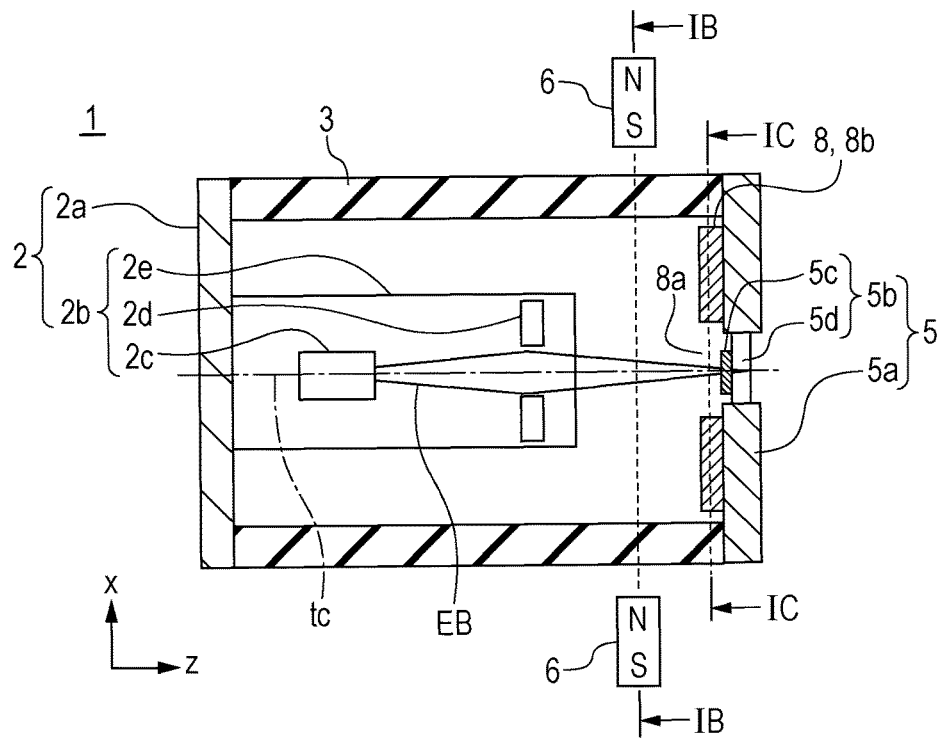
FIG. 1A is a schematic diagram and FIGS. 1B and 1C are cross-sectional views for describing a first embodiment of the present disclosure.

A transmission X-ray generation tube including a magnetic deflection portion may encounter a problem that fluctuations in the action of moving a focal position by magnetism prevents the performance of X-ray generation from recovering to a predetermined level or that the quality of radiography changes. That problem frequently arises when an image of a subject with a high relative permeability is taken with a high magnification, that is, when an image of a subject with a high relative permeability is taken at a location close to an end window.

Embodiments of the present disclosure are described below with reference to the drawings.

First Embodiment

FIGS. 1A to 1C, 5A, and 5B are schematic diagrams for describing an X-ray generation tube 1 in a first embodiment of the present disclosure.

The X-ray generation tube 1 includes an enclosure made up of a cathode 2, an anode 5, and an insulating tube 3. The inside of the enclosure is exhausted to a vacuum and its airtightness is retained to have a longer mean free path of electrons than the distance between an electron emission portion and a target.

<<Cathode>>

The cathode 2 is an electrode that defines a cathode potential of the X-ray generation tube 1 by the inclusion of a conductive cathode member 2a connected to the insulating tube 3 and an electron gun 2b and is also a structural component in the enclosure. The electron gun 2b includes a conductive tubular member 2e connected to the cathode member 2a, an electron emission portion 2c, and an electrostatic lens electrode 2d, which are disposed in the tubular member 2e. The electron emission portion 2c and electrostatic lens electrode 2d are arranged in this order in the direction from the cathode member 2a toward the anode 5 along the tube axial direction inside the tubular member 2e. The electron gun 2b is fixed to the cathode member 2a by means of the tubular member 2e. A material having strength sufficient for maintaining the vacuum of the enclosure, conductivity for defining the cathode potential of the electron gun 2b, and coefficient of linear expansion for keeping the airtight state of the insulating tube 3 is used in the cathode member 2a. Specific examples of the material of the cathode member 2a may include high melting point metals, such as molybdenum, tungsten, stainless steel, and copper.

The electron emission portion 2c may be made of a metal heat cathode, oxide cathode, impregnated cathode, or the like and may have a size of approximately $\phi$0.1 mm to $\phi$ 5 mm in the tube radial direction in accordance with the amount of X-ray tube current. Examples of the shape of the electron emission portion 2c may include a planer shape, a concave shape in a pierce electron gun, and a needle shape in a Schottky electron gun.

The electrostatic lens electrode 2d is an intermediate electrode disposed between the electron emission portion 2c and a transmission target 5b in order to define a beam profile such that electrons emitted from the electron emission portion 2c converge into a predetermined electron beam flux and a target layer 5c is irradiated with the electron beam flux. The electrostatic lens electrode 2d may be made of a metal material such as molybdenum or tungsten, as in the case of the material of the other members included in the electron gun 2b, to meet the requirement for desired heat resistance and non-magnetism, matching coefficients of linear expansion, and the like. In other words, the X-ray generation tube according to the present embodiment does not include a magnetic lens inside the X-ray generation tube 1 but includes the electrostatic lens electrode 2d in focusing a flux of electron beams emitted from the cathode 2. This form reduces the magnetization of the metal arranged inside the X-ray generation tube 1.

<<Anode>>

The anode 5 is an electrode that defines an anode potential of the X-ray generation tube 1 by the inclusion of a conductive anode member 5a connected to the insulating tube 3 and the transmission target 5b electrically connected to the anode member 5a and is also a structural component in the enclosure. The transmission target 5b includes the target layer 5c configured to emit X rays by irradiation with electrons and a supporting substrate 5d that supports the target layer 5c and that allows the generated X rays to pass therethrough to a side opposite the side on which it supports the target layer 5c. The transmission target 5b is integrated with the anode member 5a by bonding the supporting substrate 5d and anode member 5a with a brazing material disposed therebetween.

A material having a strength sufficient for maintaining the vacuum of the enclosure, conductivity for defining the anode potential of the transmission target 5b, and coefficient of linear expansion for keeping the airtight state of a bonding structure between the anode member 5a and the insulating tube 3 is used in the anode member 5a. Specific examples of the material of the anode member 5a may include high melting point metals, such as molybdenum, tungsten, stainless steel, and copper.

A predetermined radiation energy of an X ray generated in the transmission target 5b can be set by an X-ray tube voltage applied across the anode 5 and cathode 2. The X-ray tube voltage can be appropriately set in consideration of the thickness in the transmission direction, the size of a subject, the target layer 5c, the supporting substrate 5d, and the like. The X-ray tube voltage may be selected from the range of 10 kV to 200 kV.

A material having a high density and high melting point, such as tungsten, rhenium, or molybdenum, is selected for the target layer 5c in consideration of the efficiency of X-ray generation and heat resistance. The thickness of the target layer 5c may be set in the range of 0.5 μm to 15 μm to efficiently emit X rays to the outside of the tube in consideration of self-attenuation.

An allotrope of carbon, such as diamond or graphite, or a light element material, such as beryllium, may be used in the supporting substrate 5d to efficiently emit X rays generated in the target layer 5c to the outside of the tube. The thickness of the supporting substrate 5d may be set at any proper value based on the atmospheric pressure resistance capability for maintaining vacuum, X-ray transmittance, and the like and may be set in the range of 0.1 to 3 mm. The supporting substrate 5d also functions as an X-ray transmission window for enabling X rays generated in the target layer 5c to exit to the outside of the X-ray generation tube 1.

<<Insulating Tube>>

The insulating tube 3 surrounds and extends along a tube center axis tc and has a first end and a second end configured to be connected the cathode member 2a and the anode member 5a, respectively. The cathode 2 and the anode 5 are electrically insulated from each other.

The insulating tube 3 is selected such that it has an electrical insulation property, airtightness, heat resistance, and a coefficient of linear expansion matching with that of each of the cathode 2 and anode 5 and may contain, as a main ingredient, a glass material, such as multiform glass, Pyrex (registered trademark), and quartz, or a ceramic material, such as aluminum oxide or steatite.

<<Magnetic Deflection Portion>>

Next, magnetic deflection portions 6 are described with reference to FIGS. 1A to 1C and 6A to 6D.

The magnetic deflection portions 6 are arranged outside (on the outer side of) the insulating tube 3 in the tube radial direction of the X-ray generation tube 1 and between the electron emission portion 2c and transmission target 5b in the tube axial direction. Such arrangement of the magnetic deflection portions 6 enables an effective action of deflecting the trajectory by Lorentz force on electron beams EB. That is, the magnetic deflection portions 6 are arranged such that Lorentz force acts on the electron beams EB formed in the vicinity of a tube center axis tc illustrated in FIG. 1B. A magnetic material is used in the magnetic deflection portions 6. Examples of that magnetic material may include permanent magnets, such as a ferrite magnet, an alnico (aluminum, nickel, cobalt) magnet, a samarium-cobalt magnet, and a neodymium magnet, and an electromagnet.

Figure 1B:
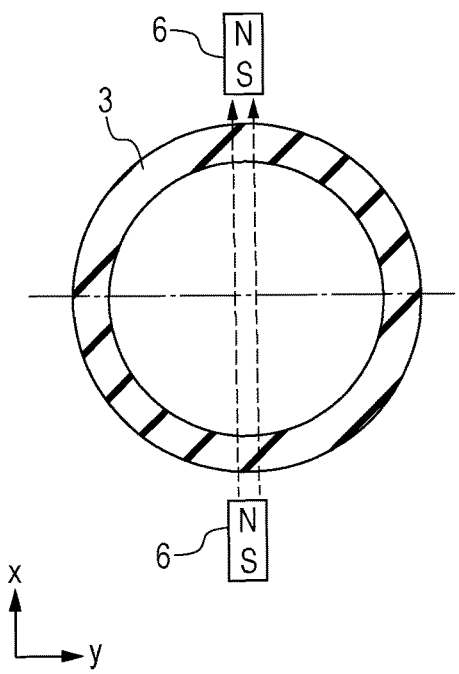
Figure 5A:
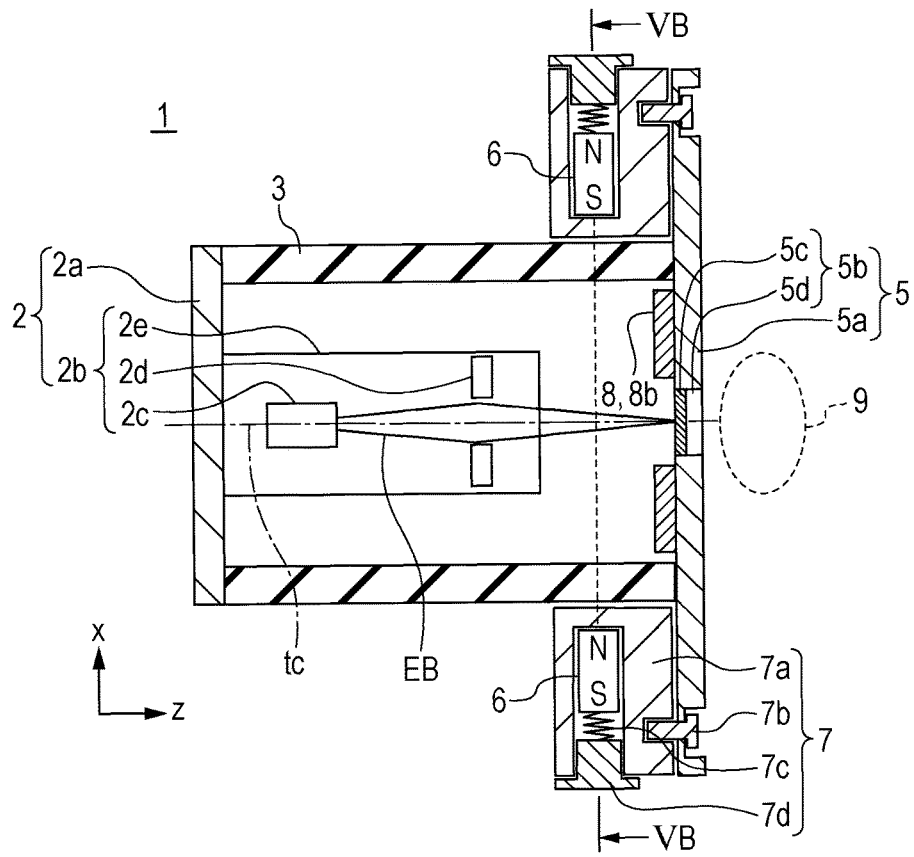
FIGS. 5A and 5B are a schematic diagram and a cross-sectional view, respectively, for describing a deflection-portion supporter according to one or more embodiments of the present disclosure.
Figure 5B:
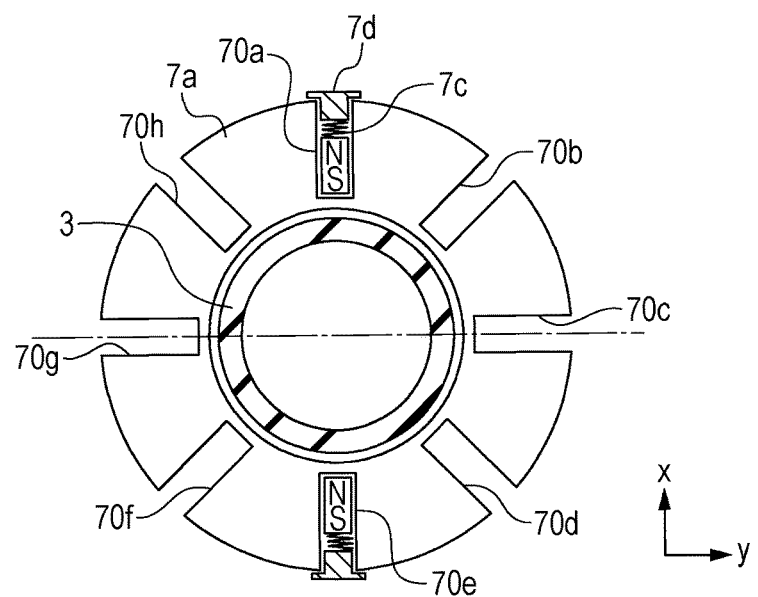

The magnetic deflection portions 6 in the present embodiment may be arranged discretely in the circumferential direction of the X-ray generation tube 1, as illustrated in FIG. 1B, such that line components of magnetic force (broken line arrows) in the tube radial direction are produced for the electron beams. In the present embodiment, the two magnetic deflection portions 6 are arranged in locations opposed to each other with the tube center axis tc located therebetween such that they are oriented so as to have polarity opposite to each other. As illustrated in FIGS. 5A and 5B, the two magnetic deflection portions 6 are supported by a deflection-portion supporter 7 connected to the anode member 5a at locations spaced 180 degrees apart from each other in the tube circumferential direction.

The deflection-portion supporter 7 in the present embodiment includes a supporting member 7a configured to support the magnetic deflection portion 6, spring members 7c configured to urge magnet sections in the magnetic deflection portions 6 inwardly in the tube radial direction, fixing members 7d configured to hold reaction forces of the spring members 7c, and connecting members 7b configured to support the supporting member 7a and connect it with the anode member 5a. The supporting member 7a has a plurality of hole portions 70a to 70h capable of housing the magnet sections in the magnetic deflection portions 6 and the spring members 7c. In the present embodiment, the position of an electronic focus can be changed in units of 45 degrees by changing the hole portions 70 for housing the magnet sections in the magnetic deflection portions 6. A form in which the deflection-portion supporter is arranged so as to be rotatable coaxially with the tube center axis tc of the insulating tube 3, not illustrated, also can change the electronic focus and is thus included in embodiments of the present disclosure.

The deflection-portion supporter 7 may be made of a non-magnetic material that has little influence on lines of magnetic force generated by the magnetic deflection portions 6. Here, the non-magnetic material indicates a material that exhibits paramagnetism or diamagnetism. When the non-magnetic material shows a relative permeability of 0.99 to 1.01, there is little influence from fluctuations in trajectory of electronic beams with respect to magnetic fields in front of the anode member 5a. The relative permeability is a dimensionless quantity calculated as $\mu/\mu_0$, where $\mu$ is a magnetic permeability of a material and $\mu_0$ is a magnetic permeability of a vacuum. Examples of the material exhibiting paramagnetism may include molybdenum, tungsten, and non-magnetic stainless steel, such as SUS 304. Examples of the material exhibiting diamagnetism may include copper and silver. The deflection-portion supporter 7 may be made of an alloy of the above-described materials. The deflection-portion supporter 7 is not limited to the structure, configuration, and the like illustrated in FIGS. 5A and 5B. The deflection-portion supporter 7 can have any structure and configuration when it can support the magnetic deflection portion 6 and control the amount of deflection and the direction of deflection of electron beams by using Lorentz force.

Figure 4A:
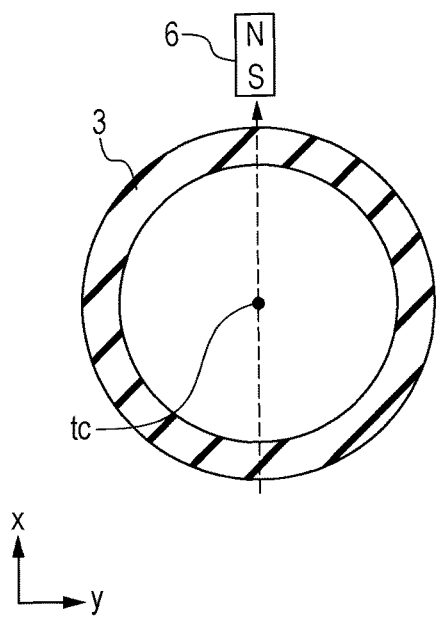
FIGS. 4A to 4D are schematic diagrams that illustrate examples of arrangement of magnet sections in a magnetic deflection portion according to one or more embodiments of the present disclosure.

FIGS. 4A to 4D illustrate variation examples of the first embodiment in which one or more magnetic deflection portions 6 are arranged in the tube circumferential direction at predetermined pitches in the anode 5. FIG. 4A illustrates a form in which one magnetic deflection portion 6 is arranged outside the tube in the tube circumferential direction such that its south pole faces the tube central axis tc so as to cause a linear line component of magnetic force to pass through an electron beam, that is, the tube central axis tc. A similar form in which one magnetic deflection portion 6 is arranged outside the tube in the tube circumferential direction such that its north pole faces the tube central axis tc so as to cause the linear line component of magnetic force to pass through the tube central axis tc is also included in embodiments of the present disclosure.

Figure 4B:
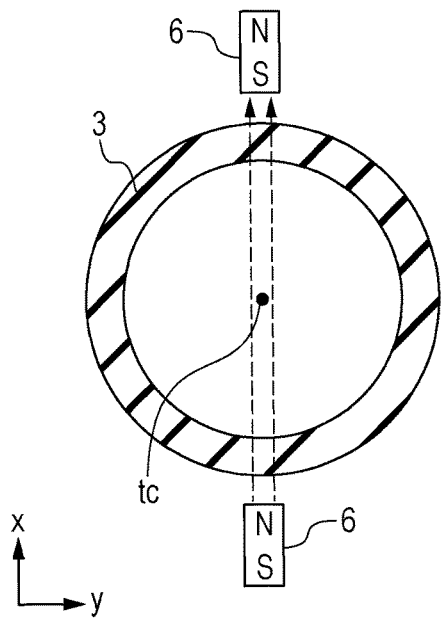

FIG. 4B illustrates a form in which the magnet sections in the magnetic deflection portions 6 are arranged such that the north pole of one magnet section faces the south pole of the other in the tube radial direction. In the present embodiment, a line component of magnetic force with high linearity can be formed in the vicinity of the tube central axis tc, and thus the offset amount (moving amount) of the electronic focus in the tube radial direction can be increased.

Figure 4C:
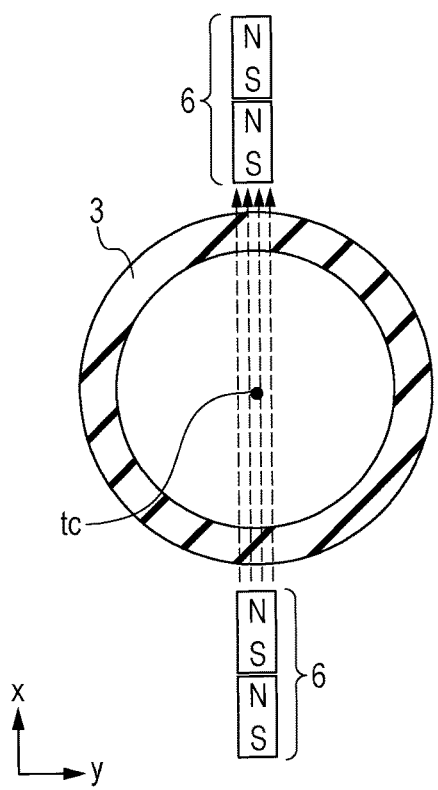
Figure 4D:
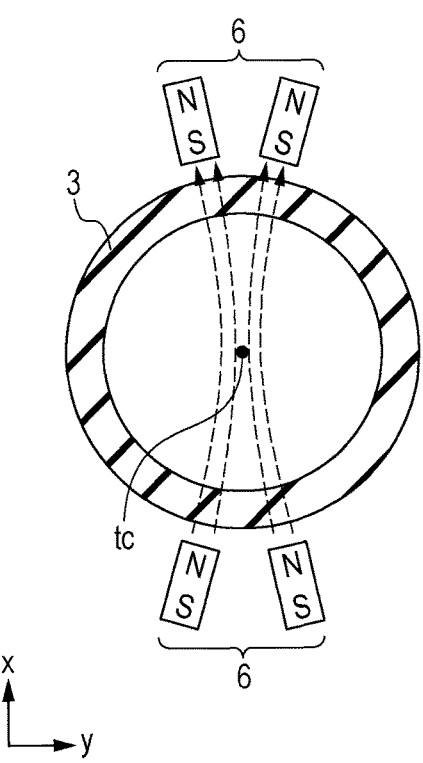

FIGS. 4C and 4D illustrate a variation example in which each of the pair of magnet sections in the magnetic deflection portions 6 illustrated in FIG. 4B includes two magnets arranged in series and that in which each of the pair of magnet sections in the magnetic deflection portions 6 includes two magnets arranged side by side, respectively. In both of the variation examples illustrated in FIGS. 4C and 4D, the amount of deflection of the electronic focus in the tube radial direction can be further increased.

The arrangement form of the magnetic deflection portions 6 may be appropriately set in consideration of the arrangement of parts included in the X-ray generation tube 1, a desired moving amount of the beam irradiation position, and the like and is not limited to the above-described examples and.

<<Magnetic Shielding Portion>>

Next, a magnetic shielding portion 8, which is a feature of the present disclosure, is described with reference to FIGS. 1A and 1C.

Figure 1C:
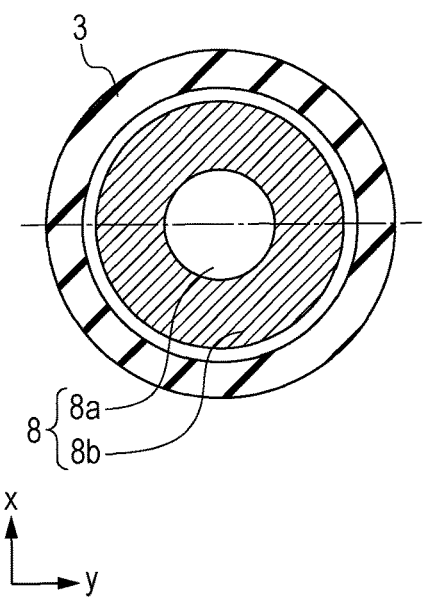

As illustrated in FIGS. 1A and 1C, the magnetic shielding portion 8 in the present embodiment is a flat-shaped annular magnetic member secured to the vacuum side of the anode member 5a so as to surround the tube center axis tc across the anode member 5a. The magnetic shielding portion 8 includes a portion that is closer to the anode 5 than the magnetic deflection portions 6 in the tube axial direction and that is arranged inside the magnetic deflection portions 6 in the tube radial direction of the X-ray generation tube 1. In other words, the magnetic shielding portion 8 is closer to the tube center axis tc than the magnetic deflection portions 6 in the tube radial direction of the insulating tube 3. The magnetic shielding portion 8 includes an aperture portion 8a opened so as to allow the electron beams EB to pass therethrough and an annular portion 8b surrounding the aperture portion 8a, as illustrated in FIG. 1C.

Figure 6A:
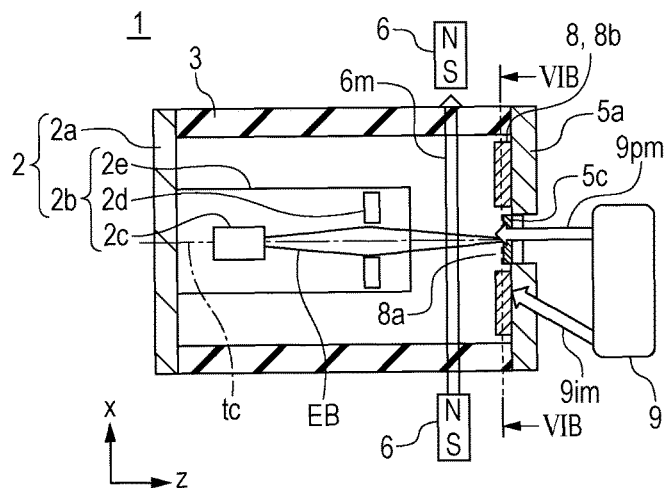
FIGS. 6A and 6B are schematic diagrams for describing a magnetic shielding effect according to one or more embodiments of the present disclosure.
Figure 6B:
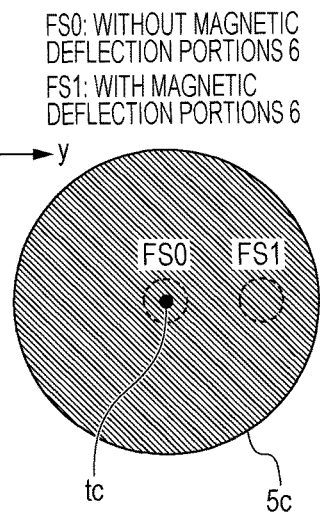
Figure 6C:
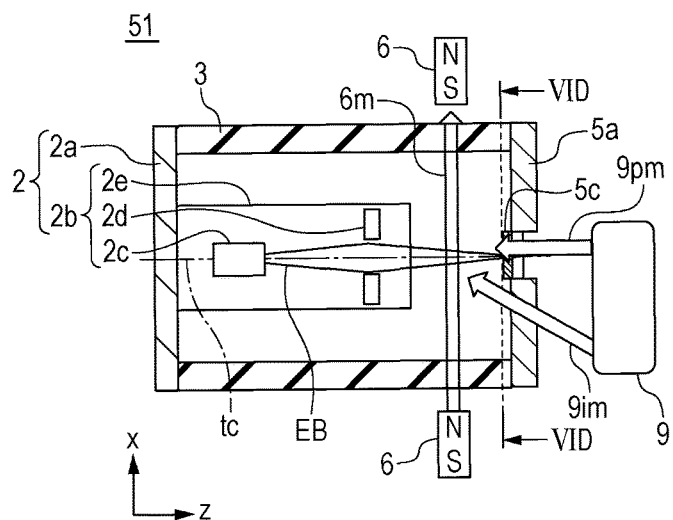
FIGS. 6C and 6D are schematic diagrams therefor in a reference example.
Figure 6D:
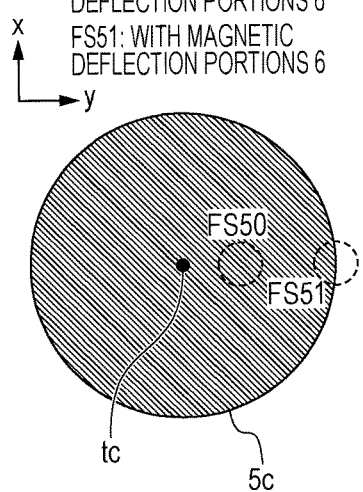

Next, the magnetic shielding effect by the magnetic shielding portion 8 is described in detail with reference to FIGS. 6A to 6D. FIG. 6A is a schematic diagram for describing interaction between lines of magnetic force (6m, 9pm, 9im) and the electron beams EB in the first embodiment. FIG. 6B is a partially enlarged view of the target layer 5c for describing the effect of moving an electronic focus FS0 in the present embodiment. FIGS. 6C and 6D are a schematic diagram and a partially enlarged view, respectively, of a reference form that differs from the first embodiment only in that the magnetic shielding portion 8 is not included.

By the arrangement of the magnetic shielding portion 8 in the present embodiment, some of the lines of magnetic force existing in an exposure region outside the tube are absorbed in the magnetic shielding portion 8, and the lines of magnetic force leaking in the vicinity of the tube center axis tc are reduced. Thus, Lorentz force on electron beams caused by the influence of the relative permeability of a subject 9, arrangement of the magnetized subject, and the like is suppressed, the position of the electronic focus can be moved by a predetermined amount of deflection, and radiographing with high reproducibility can be performed independently of the position of the X-ray generation source.

Here, a factor for the lines of magnetic force 9pm and 9im existing in the exposure region outside the tube may be the arrangement in which the magnetized subject 9 and the anode 5 are located close to each other. The magnetization of the subject 9 may be caused by magnetic fields resulting from a member with high magnetic permeability included in the subject and from the magnetic deflection portions 6. Examples of a material that has high relative permeability and that is easily magnetizable may include iron, nickel, and cobalt.

By the arrangement of the magnetic shielding portion 8 in the present embodiment, some of the lines of magnetic force 6m generated by the magnetic deflection portion 6 are absorbed in the magnetic shielding portion 8, and Lorentz force acting between the electron beams EB and the lines of magnetic force 6m is slightly reduced. However, because the magnetic shielding portion 8 is arranged so as not to block the lines of magnetic force 6m generated by the magnetic deflection portion 6 for the electron beams EB, the action of reducing the lines of magnetic force 6m by the magnetic shielding portion 8 is limited. Accordingly, as illustrated in FIG. 6B, in the form in which the magnetic shielding portion 8 is included, the electronic focus FS0 can be moved to a predetermined position FS1 by the action of the magnetic deflection portion 6 without being influenced by the external magnetic field 9pm, and thus the effective life of the transmission target 5b can be extended.

Here, the lines of magnetic force 9im, which obliquely enter the anode member 5a from the magnetic field outside the tube and exert Lorentz force on the electron beams EB in the vicinity of the tube center axis tc, are discussed. Because the annular portion 8b in the magnetic shielding portion 8 is arranged so as to block the entry of the lines of magnetic force 9im into the electron beams EB, the lines of magnetic force 9im from the subject 9 and the action of magnetizing the subject 9 by the lines of magnetic force 6m are attenuated by the magnetic shielding portion 8. Because the lines of magnetic force 9pm, which leak into the tube, and the tube axial direction tc are substantially parallel with each other at the aperture portion 8a and Lorentz force is not easily generated on the electron beams EB, the magnetic shielding portion 8 is opened in a region that intersects the tube center axis tc.

In the reference form that does not include the magnetic shielding portion illustrated in FIG. 6C, some of the lines of magnetic force 9im, which exist in the exposure region outside the tube, are not absorbed in the magnetic shielding portion and have an influence on the electron beam located in the vicinity of the tube center axis tc. Thus, because of the influence of the relative permeability of the subject 9, the arrangement of the magnetic subject 9, and the like, the position of the electronic focus is further moved by the amount corresponding to Lorentz force of the line components of magnetic force 9im entering from outside the tube, in addition to a predetermined amount of deflection. When the Lorentz force of the line components of magnetic force 9im entering from outside the tube is received, as illustrated in FIG. 6D, the electronic focus in the case with the magnetic deflection portions 6 and that without the magnetic deflection portions 6 are moved to FS51 and FS50, respectively, both of which are positions resulting from unnecessary focus movements. In this reference form, because the amount of focus movement varies, the reproducibility and stability in radiographing decrease.

As described above, in the X-ray generation tube 1 in the present embodiment, which includes the magnetic shielding portion 8, Lorentz force by the magnetic deflection portion 6 expresses the action of deflecting electron beams, and the influence of Lorentz force selectively leaking from the subject in front of the anode member 5a is reduced.

The magnetic shielding portion 8 may have a relative permeability sufficiently larger than one and may be made of a material with a relative permeability of 10 or more. Examples of the material with a high magnetic permeability include a magnetic metal being at least one selected from iron, cobalt, and nickel, silicon steel being a magnetic metal, carbon steel being a magnetic metal, magnetic stainless steel, such as SUS 420, an alloy, such as Monel, a permanent magnet, such as a ferrite magnet and a permalloy magnet, and combinations of them.

The magnetic permeability $\mu$ of a material can be calculated from $\mu=B/H$ by detecting a magnetic flux density B of a magnetic field H generated by feeding a current through a coil in which the material is inserted with a magnetic sensor or the like. Examples of the magnetic sensor for detecting the magnetic flux density may include a Hall element, a magnetoresistive element, a magnetic impedance element, and a superconducting quantum interference device (SQUID). In general, the magnetic shielding effect increases with an increase in $\mu \times d$ [H], which is the product of the magnetic permeability $\mu$ [H/m] of the magnetic shielding portion 8 and the thickness d [m]. The product $\mu \times d$ [H] may be equal to or larger than $1 \times 10^{-8}$ and equal to or smaller than $1 \times 10^{-4}$. When the magnetic shielding effect is increased, the lines of magnetic force 6m for the electron beams EB are also reduced, and the amount of deflection of the electron beams is reduced. Thus, the range of $\mu \times d$ [H] may be from $1 \times 10^{-7}$ to $1 \times 10^{-5}$. In the present specification, the thickness d is defined as the length along the tube axial direction (Z direction in FIG. 1A).

The type and arrangement of the magnets in the magnetic deflection portions 6 may be appropriately set in consideration of the material, thickness, and shape of the magnetic shielding portion 8, a desired moving amount of the beam radiation position, and the like and are not limited to the above-described examples.

Second Embodiment

Figure 2A:
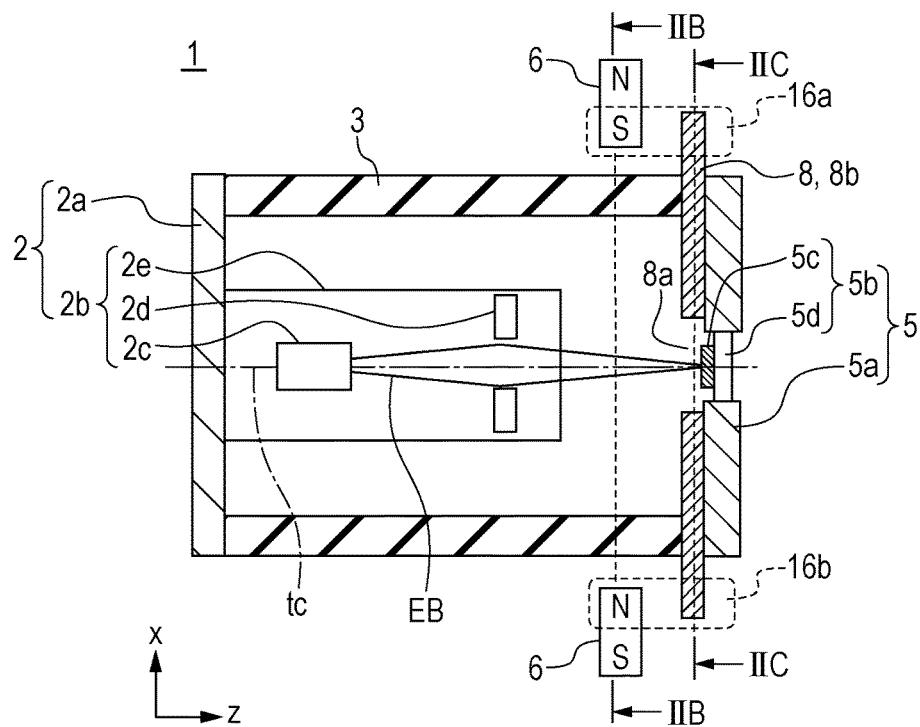
FIG. 2A is a schematic diagram and FIGS. 2B and 2C are cross-sectional views for describing a second embodiment of the present disclosure.
Figure 2B:
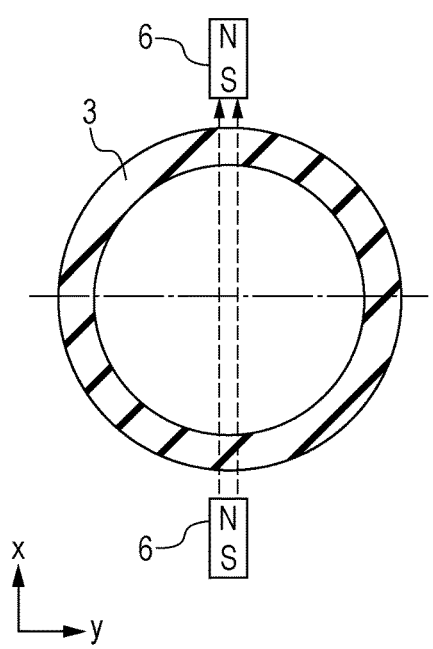
Figure 2C:
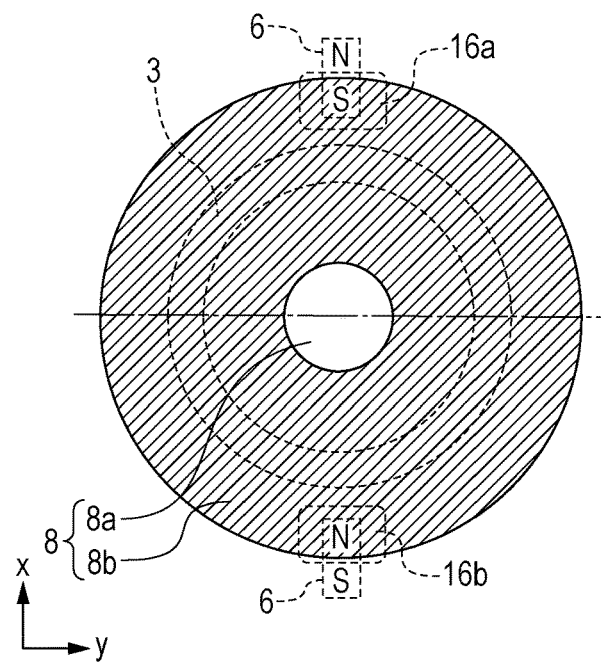

FIGS. 2A to 2C are schematic diagrams for describing the X-ray generation tube 1 according to a second embodiment of the present disclosure. The second embodiment differs from the first embodiment in that when seen along the tube axial direction, the magnetic shielding portion 8 includes portions 16a and 16b overlapping the magnetic deflection portions 6 in the tube radial direction, as illustrated in FIGS. 2A to 2C. The overlapping portions 16a and 16b are hermetically connected to the insulating tube 3.

In the present embodiment, as illustrated in FIGS. 2A to 2C, the magnetic shielding portion 8 includes the overlapping portions 16a and 16b, which overlap the magnetic deflection portions 6 along the tube radial direction. This leads to the magnetic shielding effect larger than that in the first embodiment. The position stability of the X-ray generation source can be further enhanced independently of the relative permeability of the subject 9, the position of photographing, and the like.

Third Embodiment

Figure 3A:
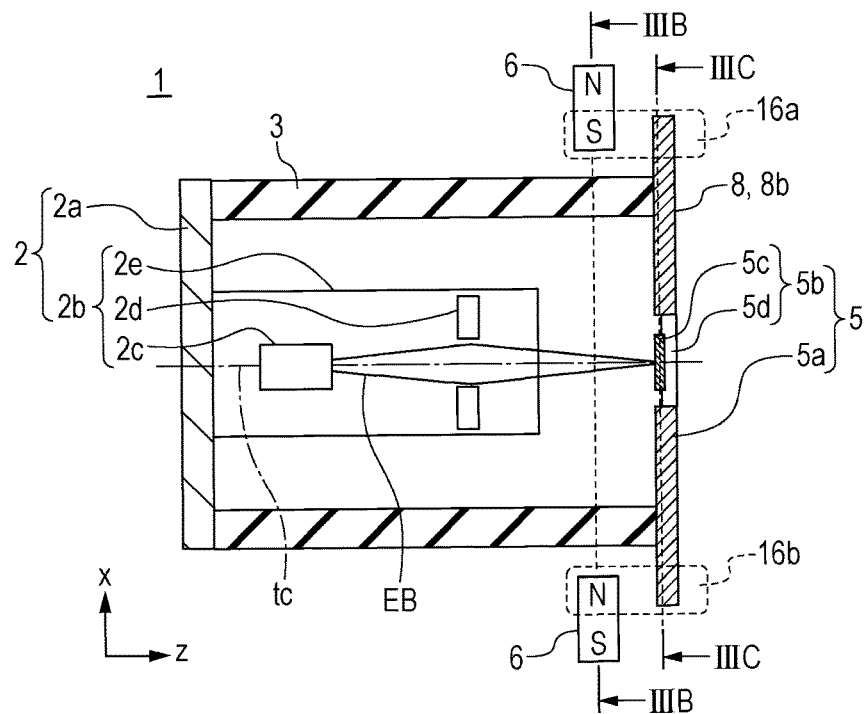
FIG. 3A is a schematic diagram and FIGS. 3B and 3C are cross-sectional views for describing a third embodiment of the present disclosure.
Figure 3B:
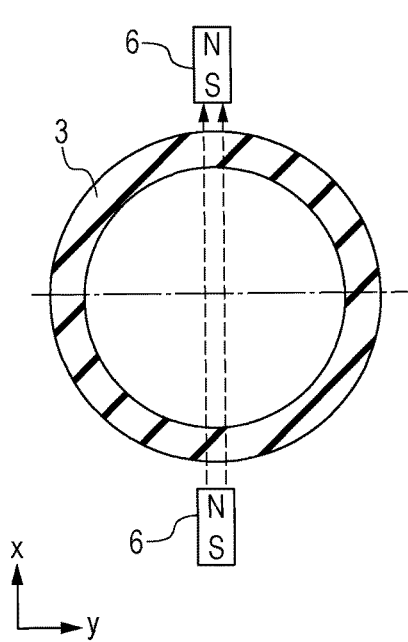
Figure 3C:
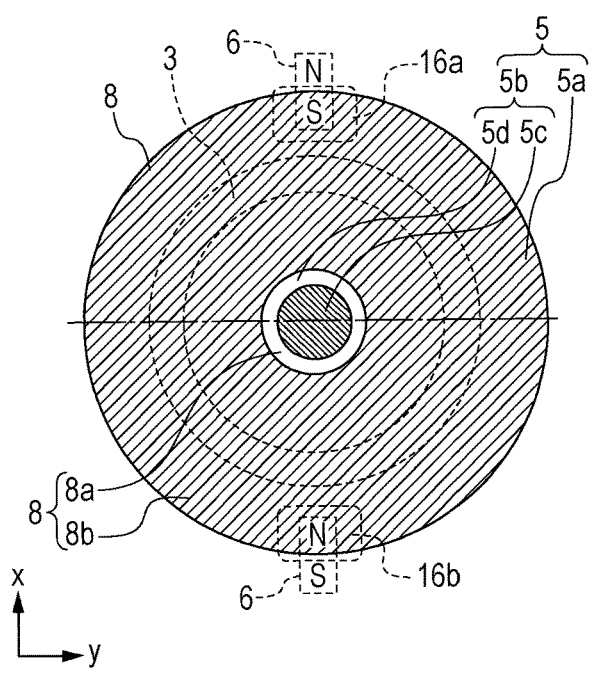

FIGS. 3A to 3C are schematic diagrams for describing the X-ray generation tube 1 according to a third embodiment of the present disclosure. The third embodiment is the same as the first embodiment, except that the anode member 5a is made of a material with a magnetic shielding property, as illustrated in FIGS. 3A to 3C.

The magnetic shielding portion 8 relates to the anode 5 in the first to third embodiments. It may be an intermediate electrode (not illustrated) insulated from the anode member. In the form in which the magnetic shielding portion is insulated from the anode member, the magnetic shielding portion may be arranged inside the enclosure and arranged closer to the electron emission portion than the anode member in the tube axial direction to suppress discharging.

Fourth Embodiment

Figure 7:
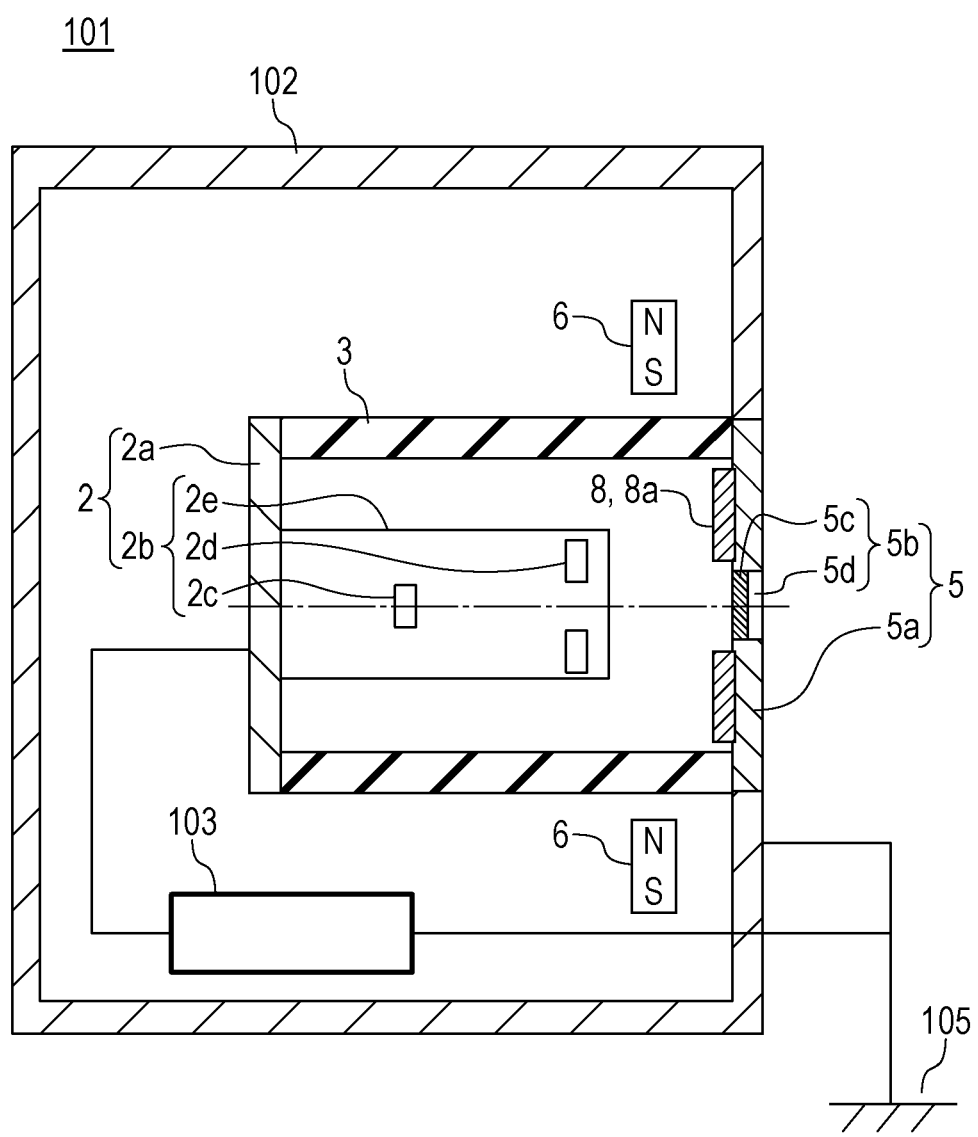
FIG. 7 is a schematic diagram for describing an X-ray generation apparatus according to one or more embodiments of the present disclosure.

FIG. 7 is a diagram of an X-ray generation apparatus 101 according to a fourth embodiment of the present disclosure. The X-ray generation apparatus 101 includes the X-ray generation tube 1 according to the first embodiment, a driving circuit 103 configured to drive the X-ray generation tube 1, and a container 102 configured to house them.

The driving circuit 103 includes a tube voltage circuit (not illustrated) configured to apply a tube voltage across the anode 5 and cathode 2 and an electronic-gun driving circuit (not illustrated) configured to drive the electron gun 2b such that it emits an electron beam with a predetermined exposure strength and for a predetermined period of exposure time. A remaining space in the container 102 other than the driving circuit 103 and X-ray generation tube 1 is filled with an insulating fluid (not illustrated). Examples of the insulating fluid may include an insulating oil, such as a mineral oil and a silicone oil, and an insulating gas, such as sulfur hexafluoride ($SF_6$). The anode 5 is grounded to an earth 105 with the container 102 disposed therebetween. Accordingly, the X-ray generation apparatus 101 with stability of the position of the X-ray generation source enhanced independently of the relative permeability of the subject, the position of photographing can be achieved.

Fifth Embodiment

Figure 8:
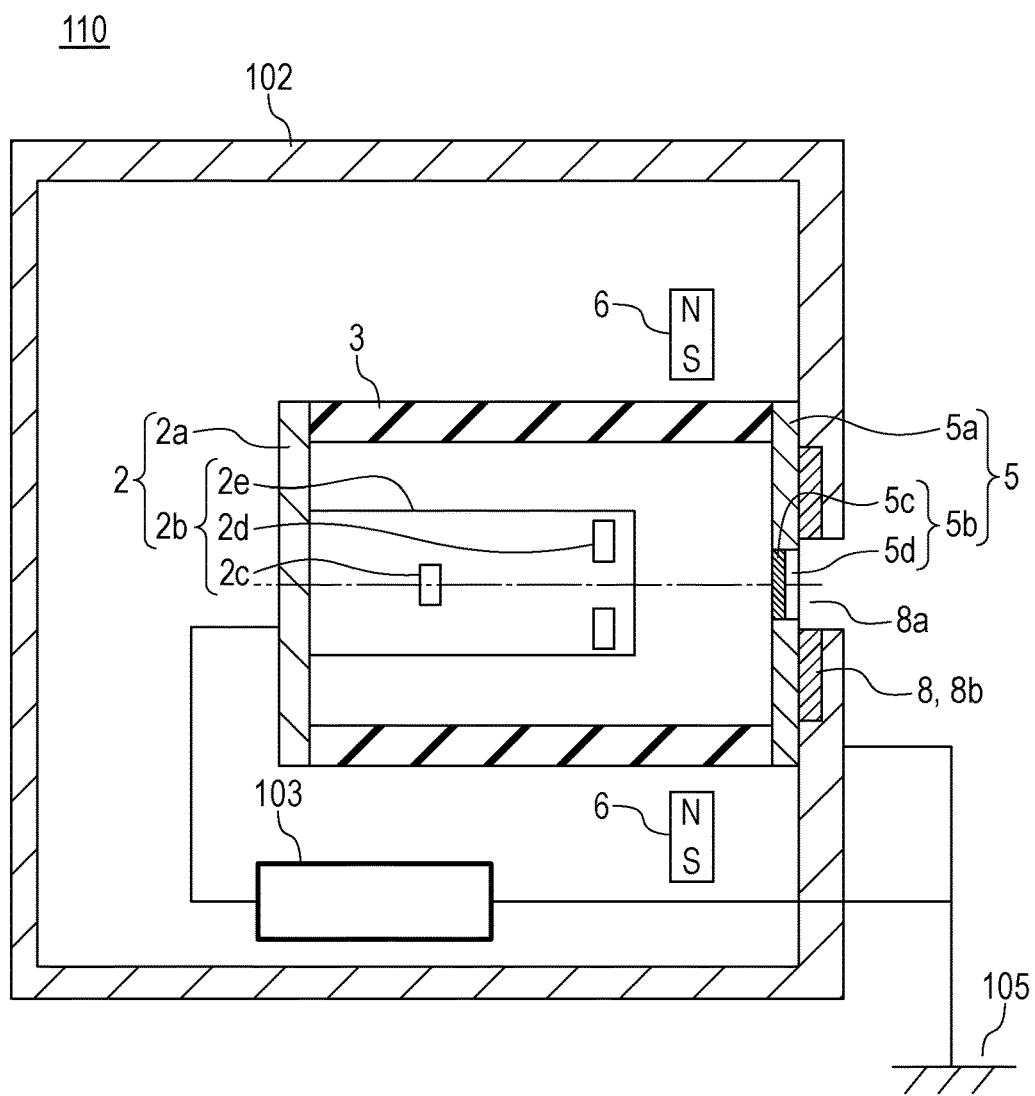
FIG. 8 is a schematic diagram for describing an X-ray generation apparatus according to one or more embodiments of the present disclosure.

FIG. 8 is a diagram that illustrates the configuration of an X-ray generation apparatus 110 according to a fifth embodiment of the present disclosure. The X-ray generation apparatus 110 differs from the X-ray generation apparatus 101 in the fourth embodiment in that the magnetic shielding portion 8 is not included in the X-ray generation tube but is fixed in a part of the container 102. In the present embodiment, the magnetic shielding portion 8 is fixed to the container 102. A form in which the magnetic deflection portion 6 is fixed to the container 102 is also included in the present disclosure.

Sixth Embodiment

Figure 9:
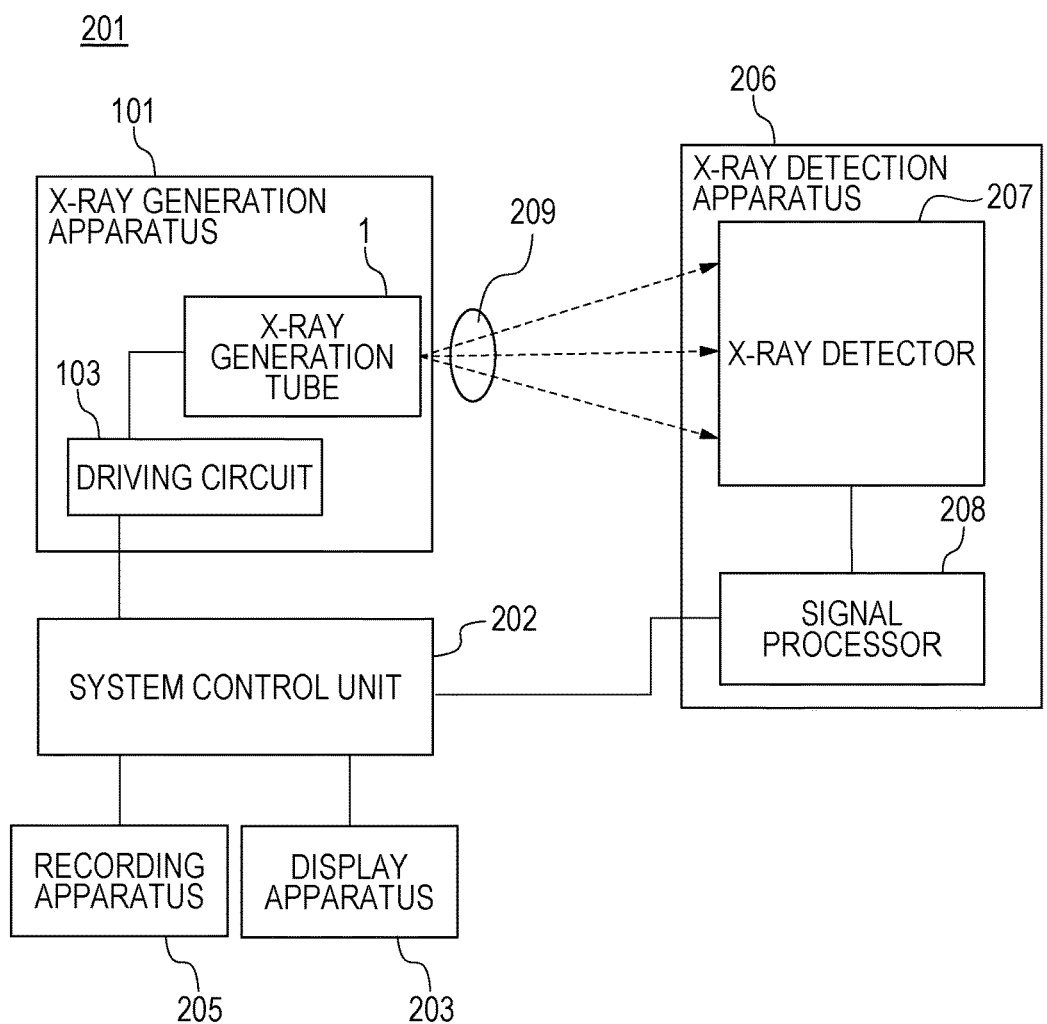
FIG. 9 is a schematic diagram for describing a radiography system according to one or more embodiments of the present disclosure.

FIG. 9 is a block diagram of a radiographing system 201 according to a sixth embodiment of the present disclosure. A system control unit 202 controls the X-ray generation apparatus 101 described in the fourth embodiment and an X-ray detection apparatus 206 in coordination with each other. The X-ray detection apparatus 206 includes an X-ray detector 207 and a signal processor 208. X rays emitted from the X-ray generation apparatus 101 are controlled based on control signals output from the system control unit 202 to the X-ray generation apparatus 101. An X ray emitted from the X-ray generation apparatus 101 passes through a subject 209 and is detected by the X-ray detector 207. The X-ray detector 207 converts the detected X ray into an image signal and outputs it to the signal processor 208. The signal processor 208 performs predetermined signal processing on the image signal under control by the system control unit 202 and outputs the processed image signal to the system control unit 202. The system control unit 202 outputs a display signal for displaying an image on a display apparatus 203 based on the processed image signal to the display apparatus 203 and retains image data in a recording apparatus 205. The display apparatus 203 displays the image based on the display signal on a screen as am obtained image of the subject 209.

Accordingly, the radiography system with high reproducibility and high stability in photographing quality can be established independently of the relative permeability of the subject 9, the position of photographing, and the like.

Advantages

With the X-ray generation tube according to the present disclosure, because the magnetic shielding portion absorbs lines of magnetic force, lines of magnetic force generated by the magnetic deflection portion do not easily extend to the side of the subject, which is the target of exposure, and magnetization of the subject by a deflected magnetic field generated by the magnetic deflection portion is limited. Thus, in the cases where a large image of a subject with high relative permeability is taken, because Lorentz force exerted on an electron beam trajectory by the subject is limited and the fluctuations in the electron beam focus are suppressed, radiographing can be performed with stability.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-102863 filed May 23, 2016, which is hereby incorporated by reference in its entirety.

What is claimed is:

1. An X-ray generation tube comprising:
    a cathode including an electronic gun and a cathode member configured to hold the electronic gun;
    an anode including a transmission target configured to be irradiated with electrons and generate an X ray and an anode member configured to hold the transmission target;

an insulating tube surrounding and extending along a tube center axis and including a first end and a second end configured to be connected to the cathode and the anode, respectively;

at least one magnetic deflection portion disposed outside the insulating tube in a tube radial direction and arranged between the cathode and the anode in a tube axial direction; and a magnetic shielding portion including a portion that is closer to the transmission target than the magnetic deflection portion in the tube axial direction and that is closer to the tube center axis than the magnetic deflection portion in the tube radial direction.

2. The X-ray generation tube according to claim 1, wherein: the magnetic shielding portion further includes a portion that overlaps the magnetic deflection portion in the tube radial direction as seen from the tube axial direction.

3. The X-ray generation tube according to claim 1, wherein:

a product μ×d [H] is in a range of $1 \times 10^{-8}$ to $1 \times 10^{-4}$, where μ is a magnetic permeability [H/m] of the magnetic shielding portion and d is a thickness thereof in the tube axial direction.

4. The X-ray generation tube according to claim 1, wherein: the magnetic shielding portion shows a relative permeability of 10 or more.

5. The X-ray generation tube according to claim 1, wherein: the magnetic shielding portion contains any of a magnetic metal being at least one selected from iron, cobalt, and nickel, silicon steel being a magnetic metal, carbon steel being a magnetic metal, magnetic stainless steel, ferrite, and permalloy.

6. The X-ray generation tube according to claim 1, wherein: the magnetic deflection portion includes at least one of a ferrite magnet, an alnico (aluminum, nickel, and cobalt) magnet, a samarium-cobalt magnet, and a neodymium magnet, and an electromagnet.

7. The X-ray generation tube according to claim 1, wherein: the at least one magnetic deflection portion comprises a plurality of magnetic deflection portions spaced at predetermined pitches in a tube circumferential direction.

8. The X-ray generation tube according to claim 1, further comprising: a deflection-portion supporter disposed outside the insulating tube, arranged between the cathode and the anode in the tube axial direction, and configured to support the magnetic deflection portion.

9. The X-ray generation tube according to claim 8, wherein: the deflection-portion supporter includes a plurality of portions capable of housing the magnetic deflection portion.

10. The X-ray generation tube according to claim 8, wherein: the deflection-portion supporter is arranged so as to be rotatable coaxially with the tube center axis of the insulating tube.

11. The X-ray generation tube according to claim 8, wherein: the deflection-portion supporter shows a relative permeability in a range of 0.99 to 1.01.

12. The X-ray generation tube according to claim 8, wherein: the deflection-portion supporter is made of a material exhibiting paramagnetism or diamagnetism.

13. The X-ray generation tube according to claim 8, wherein: the deflection-portion supporter contains at least one of molybdenum, tungsten, non-magnetic stainless steel, copper, and silver.

14. The X-ray generation tube according to claim 1, wherein: the transmission target includes a target layer configured to generate X rays by irradiation with electrons and a supporting substrate configured to support the target layer and allow X rays generated in the target layer to pass therethrough.

15. The X-ray generation tube according to claim 1, wherein: the electronic gun includes an electron emission portion and an electrostatic lens electrode configured to cause electrons emitted from the electron emission portion to converge into a predetermined electron beam flux.

16. An X-ray generation apparatus comprising:
the X-ray generation tube according to claim 1;
a driving circuit configured to apply a voltage across the anode and the cathode; and
a container configured to house the X-ray generation tube and the driving circuit.

17. A radiography system comprising:
the X-ray generation apparatus according to claim 16;
an X-ray detector configured to detect an X ray emitted from the X-ray generation apparatus and passing through a subject; and
a control unit configured to control the X-ray generation apparatus and the X-ray detector in coordination with each other.

18. An X-ray generation apparatus comprising:
an X-ray generation tube including:
a cathode including an electronic gun and a cathode member configured to hold the electronic gun;
an anode including a transmission target configured to be irradiated with electrons and generate an X ray and an anode member configured to hold the transmission target; and
an insulating tube surrounding and extending along a tube center axis and including a first end and a second end configured to be connected to the cathode and the anode, respectively;
at least one magnetic deflection portion disposed outside the insulating tube in a tube radial direction and arranged between the cathode and the anode in a tube axial direction;
a magnetic shielding portion including a portion that is closer to the anode than the magnetic deflection portion in the tube axial direction and that is closer to the tube center axis than the magnetic deflection portion in the tube radial direction; and
a container configured to house the X-ray generation tube and the magnetic shielding portion,
wherein the magnetic shielding portion is fixed to the container.

19. The X-ray generation apparatus according to claim 18, wherein the magnetic deflection portion is fixed to the container.

20. A radiography system comprising:
the X-ray generation apparatus according to claim 18;
an X-ray detector configured to detect an X ray emitted from the X-ray generation apparatus and passing through a subject; and
a control unit configured to control the X-ray generation apparatus and the X-ray detector in coordination with each other.

* * * * *